(12) United States Patent
Arn

(10) Patent No.: US 7,846,116 B2
(45) Date of Patent: Dec. 7, 2010

(54) METHOD AND DEVICE FOR FIXATION OF THE HEAD OF A PATIENT

(75) Inventor: Thomas Arn, Lidingö (SE)

(73) Assignee: Elekta AB (Publ), Stockholm (SE)

( * ) Notice: Subject to any disclaimer, the term of this patent is extended or adjusted under 35 U.S.C. 154(b) by 785 days.

(21) Appl. No.: 11/578,784

(22) PCT Filed: Apr. 27, 2005

(86) PCT No.: PCT/SE2005/000600

§ 371 (c)(1),
(2), (4) Date: Nov. 21, 2006

(87) PCT Pub. No.: WO2005/104975

PCT Pub. Date: Nov. 10, 2005

(65) Prior Publication Data

US 2008/0195011 A1    Aug. 14, 2008

(30) Foreign Application Priority Data

Apr. 30, 2004    (SE) .................................. 0401160

(51) Int. Cl.
*A61F 5/00*    (2006.01)
*A61B 17/00*    (2006.01)
*A61B 17/60*    (2006.01)
(52) U.S. Cl. .............................. 602/17; 606/54; 606/59
(58) Field of Classification Search ................... 602/17, 602/18; 606/54, 59, 61, 130, 62, 72, 56; D24/127
See application file for complete search history.

(56) References Cited

U.S. PATENT DOCUMENTS

| 4,612,930 | A |   | 9/1986  | Bremer |
|-----------|---|---|---------|--------|
| 5,042,462 | A |   | 8/1991  | Bremer |
| 5,062,415 | A | * | 11/1991 | Weatherby et al. ............. 602/17 |
| 5,156,588 | A | * | 10/1992 | Marcune et al. ............... 602/17 |
| 5,197,965 | A |   | 3/1993  | Cherry et al. |

FOREIGN PATENT DOCUMENTS

WO        WO 03094769 A      11/2003

* cited by examiner

*Primary Examiner*—Kim M Lewis
(74) *Attorney, Agent, or Firm*—Buchanan Ingersoll & Rooney PC

(57)    ABSTRACT

The present invention relates to a device for fixation to a head of a patient during neurological diagnosis, therapy or surgery, in particular during MRI diagnosis. The device comprises at least one fixation pin for fixation to the head, a sleeve member (5) having an internal threaded through bore to at least partly receive and hold said fixation pin, and a pin support member for supporting said fixation pin and sleeve member. The sleeve member is exchangeable and provided in at least two different lengths in order to allow adaptation of the sleeve member to the size of the head to improve the fixation of the head and avoid the fixation pin to protrude beyond the outer boundary of the pin support member. The invention also relates to a method for fixation of a head.

18 Claims, 2 Drawing Sheets

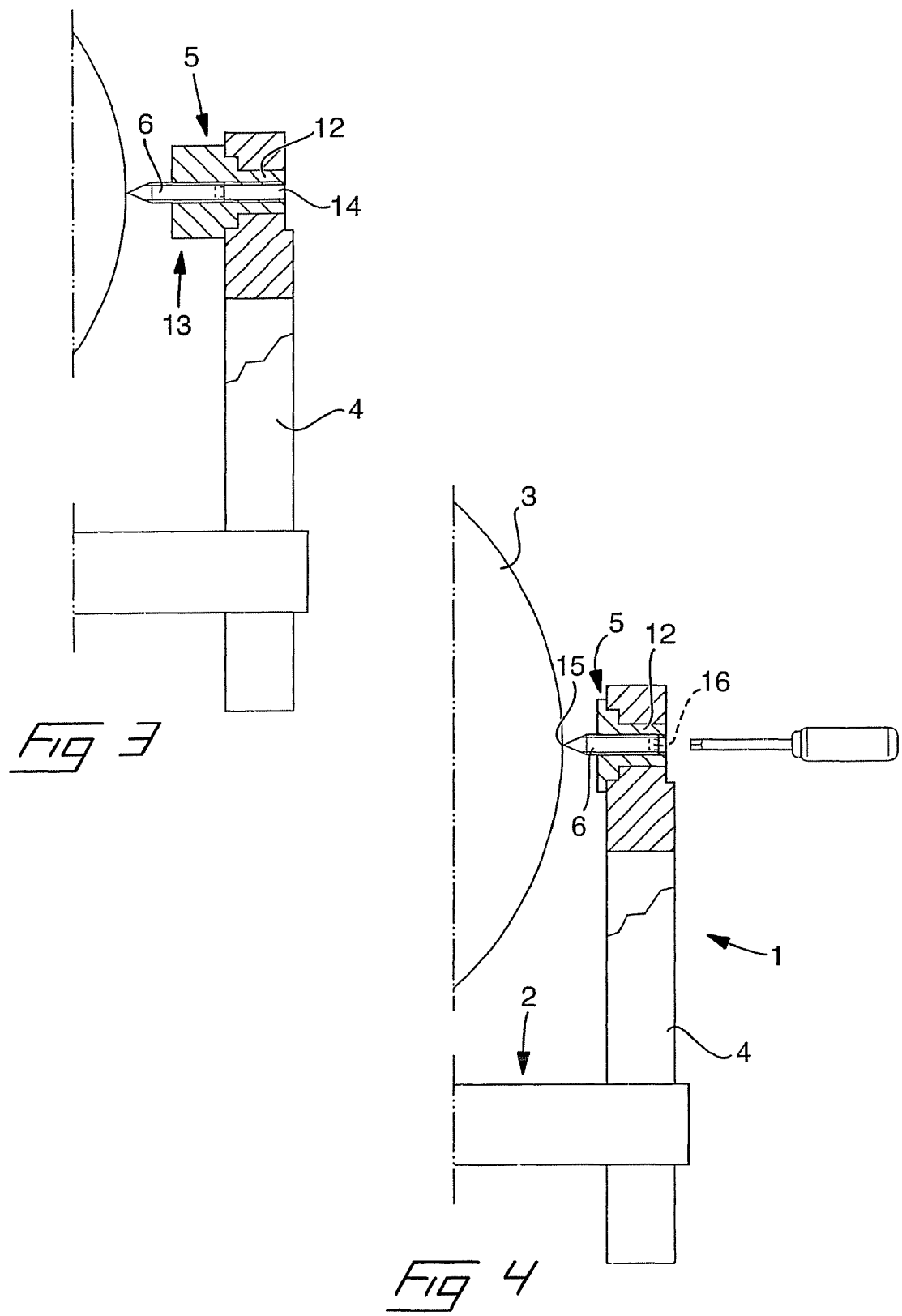

METHOD AND DEVICE FOR FIXATION OF THE HEAD OF A PATIENT

FIELD OF THE INVENTION

The present invention relates to a device for fixation of a head of a patient during neurological diagnosis, therapy or surgery, in particular during MRI diagnosis. The device comprises at least one fixation pin for fixation to the head of a patient, and at least one pin support member for supporting said fixation pin.

The invention also relates to a method for fixation of a head of a patient during neurological diagnosis, therapy or surgery, by means of a device mentioned above.

BACKGROUND OF THE INVENTION

During neurological surgery, therapy or diagnosis, it is common practice to work with a reference system being fixed in relation to the head of the patient using some type of fixation device. The reference system is used to determine the location of different areas in the involved part/tissue of the patient.

An example of such a reference system is a so-called stereotactic frame provided with pin support members in form of posts having fixation pins for invasive fixation to the skull of a patient. In use during for example MRI (Magnetic Resonance Imaging) diagnostics, the stereotactic frame is arranged around the head of a patient, and the fixation pins of the posts connected to the frame are screwed into or to abutment against the bone of the skull, thus ensuring a rigid fixation of the reference system. The frame is then rigidly held in position in relation to a MRI table.

The PCT-application SE 03/00723 discloses a fixation device comprising a pin support member. Besides a pin support member and a fixation pin, this fixation device comprises a sleeve shaped insulation means which is arranged to be supported on the pin support member and at least partly surround and hold the fixation pin. This is done to restrict the electrical coupling between the pin support member and the fixation pin when those are made of electrically conductive materials, and thus prevent temperature rise in the pins and the areas around them, such as the tissue of the head, due to the electrical coupling.

A problem associated with prior art fixation devices is that the fixation pins in most cases protrude a distance beyond the outer boundaries of the pin support members. This is sometimes due to the fact that the fixation pins are provided with external engagement means on their outer ends, to be engaged when threading them to or from a fixation position, which preclude completely screwing in of the fixation pins into the pin support members. Also in the case where the fixation pin is provided with internal engagement means on its outer end, it is common that the fixation pin extends through the entire pin support member and protrudes on the outer side of the pin support member, due to the need for sufficient support for the fixation pin from the pin support member and the absence of fixation pins having correctly adapted length. Such protruding ends of the fixation pins may interfere with the equipment and apparatuses used during the diagnosis, therapy or surgery.

Moreover, the frame members used are usually provided in only one size to reduce the costs, and designed to be able to receive the largest expected size of head. This has to result that when fixation of a small and a more common medium sized head, there will be needed exceedingly long fixation pins to be able to secure the head. Long fixation pins may be desirable also when displacing the head in relation to the reference system in order to reach peripheral disposed target areas in the head.

The use of the long fixation pins for holding the weight of the head, give rise to a large bending moment, which has to effect that the deflection, of even high quality fixation pins, will be comparatively large. The fixation thus becomes unstable with an obvious risk that the target area for treatment may become considerably displaced in relation to the reference system from the point of time when generating an image of the target area until treatment.

As a rule it is namely common practice that an image will in a first step be generated of the target area. During analysis of the image and deciding upon the best way for treatment, the patient will be disconnected from the image generating apparatus, which normally is a MRI or a CT but which also may be a X-ray, PET or MEG apparatus, but will still have the fixation device secured to the head by means of the fixation pins. When the treatment are to begin, the patient will be connected to a different equipment for surgery, radiation or other type of treatment, and it is then extremely important that the head will be secured in exactly the same position in relation to the reference system and the equipment as when generating the image, in order to achieve effective treatment of the relevant parts of the brain and prevent treatment of healthy parts.

Different load conditions, which can lead to displacement of the head in relation to the reference system, may occur between the image generating occasion, which in most cases is performed with the patient lying on the back, and the occasion of treatment when the patient may be placed in a different position, e.g. sitting. In most cases a divergence of less than about 0.1 mm is desirable.

To allow fixation of heads of all different sizes, it is also necessary to provide fixation pins in many different lengths. It is not unusual that twenty or more different lengths of fixation pins have to be provided. Of course this makes the fixation device more expensive to produce and more intricate to use.

SUMMARY OF THE INVENTION

It is an object of the present invention to eliminate the above mentioned problems associated with prior art techniques and provide a method for fixation as well as a fixation device, which ensure a reliably fixation of a patient's head during diagnosis, therapy or surgery without having the outer ends of the fixation pins protruding beyond the pin support members and without the need for an excessive number of fixation pins of different lengths.

Accordingly, the present invention is based on the insight that the above mentioned object may be achieved by a method and a device in which the sleeve member in the pin support member extends inwards from said pin support member towards the head to protrude beyond the inner boundary of said pin support member. This has to effect that the free protruding length of each fixation pin in the region between the sleeve member and the head, may be kept reasonable with regard to the bending moment exerted on the fixation pin due to the weight of the head, and a reduction of the possible risk of deflection of the fixation pin because of that. Since the sleeve member can be made with a considerable larger cross section than the fixation pin, the sleeve member are much more well adapted to take up the forces involved without any significant deflection.

In a second aspect of the invention, the sleeve member is exchangeable between sleeve members of different lengths. In this way it is possible to adapt the distance between the inner end of the sleeve member and the head to be within a preferred range, e.g. within 0-30 mm, preferably 0-20 mm and most preferred 0-10 mm.

The fixation pin is adapted to be completely threaded into the sleeve member to ensure that it do not protrude beyond the outer side of the sleeve member and the pin support member so as not to interfere with apparatuses or equipment for diagnosis, therapy or surgery. The available space in the different apparatuses for diagnostic or treatment, is often critical since the head as a rule is displaced until the target area is placed in the fixed focus area of the apparatus. The first items that comes into contact with the interior of the apparatus, will be the fixation pins if they protrude outwards from the fixation device. For this reason the fixation pin do not present any external engagement means. Instead the engagement means is formed as an internal engagement means, e.g. a slot or a polygonal structure, such as a hexagonal bore, for seating of a screw driver in the outer end of the fixation pin.

The sleeve member may be made of any arbitrary material having suitable properties. To restrict the electrical coupling between a possible metal pin support member and a metal fixation pin, it is however preferred that the sleeve member being made of an electrical insulating material such as plastics or ceramics. The sleeve member may also be made as a disposable part, which is discarded after one use, or as a reusable part which preferably may be sterilized after each use, whichever is most desired.

Sometimes it is also desirable to make use of fixation pins made of plastics, possibly in combination with metal casings. In these cases the fixation pins are less adapted to take up bending moments in comparison with metal fixation pins and, accordingly, the need for support of the pins even larger.

According to the invention, each fixation device is provided with at least one length of sleeve member as well as at least one length of fixation pin. However, in a preferred embodiment the fixation device comprises two to five different lengths of sleeve members and two to five different lengths of fixation pins. For most applications this will be satisfactory. The method and the device according to the invention, may however include the use of more than those mentioned numbers of different lengths of sleeve members and fixation pins, respectively.

The sleeve member may be secured to the pin support member in any arbitrary suitably way, as for example in a seating or a receiving formation on top or at one of the sides of the pin support member. In a preferred embodiment however, the pin support member comprises a receiving formation in form of a trough hole in the pin support member, in which the sleeve member is inserted.

In the seated position the sleeve member must be attached to the pin support member in such a way that it is prevented from being accidentally removed from the pin support member in an axial direction inward, toward the tip of the fixation pin, although it is not necessary for it to be locked in this direction since the screwing in of the fixation pin toward the head of the patient will press the sleeve member in the outward direction. However, in the axial outward direction, away from the tip of the fixation pin, the sleeve member has to have a seated position so as to be able to press the fixation pin towards the patient's head. In the seated position, the sleeve member must also be locked against rotational movement since the fixation pin will be rotationally screwed into the sleeve member. The attachment can be achieved in different ways, such as by press fit or snap fit of the sleeve member into the pin support member including some kind of rotational preventing engagement between the sleeve member and the pin support member. The sleeve member could also be threaded coupled to the pin support member if some kind of rotation preventing means is arranged in the seated position.

A fixation device according to the invention, comprises normally one pin support member, one or more sleeve members and one or more fixation pins. At least three such fixation devices may be assembled together with a frame member, e.g. a stereotactic frame, to achieve a fully rigid fixation of a head. However, the pin support member need not, as in the embodiment shown in the accompanying drawings, necessarily be in the shape of a post 3. It is also feasible to arrange the sleeve members directly on a frame member, in which case said frame member constitutes the pin support member.

As used herein, the terms inner, inwards etc., refers to a position and a direction toward the head, whereas the terms outer, outwards etc., refers to a position and a direction away from the head.

Further advantages of the invention will appear by way of example in connection with the following description of a preferred embodiment, referring to the accompanying drawings in which:

BRIEF DESCRIPTION OF THE DRAWINGS

FIGS. 3 and 4 are partly cross sections through a frame member and a fixation device provided with sleeve members of different lengths for fixation of heads of different sizes.

DESCRIPTION OF A PREFERRED EMBODIMENT

Figure 1:
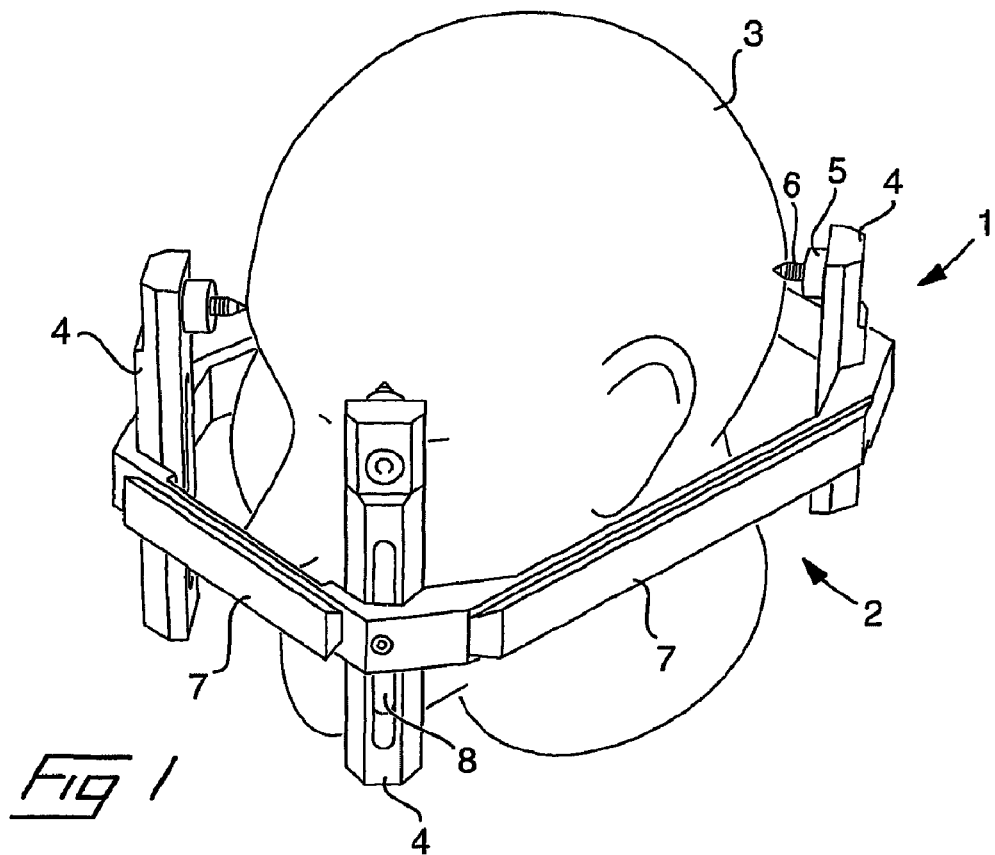
FIG. 1 shows a fixation device according to an embodiment of the invention when in use in a stereotactic frame attached to a patient.

FIG. 1 shows a fixation device 1 according to an embodiment of the invention when in use with a stereotactic frame 2 and fixed to the head 3 of a patient.

The fixation device 1 in this embodiment comprises four pin support members 4, of which only three are visible in FIG. 1. Each of the four pin support members 4 carries a sleeve member 5 and a fixation pin 6 and are arranged in the corners of a rectangular stereotactic frame 2 comprising four frame parts 7.

Figure 2:
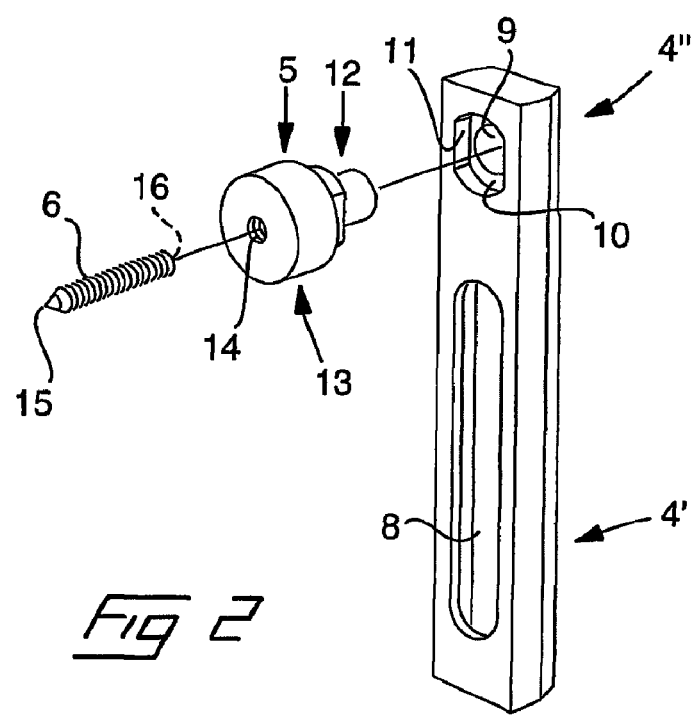
FIG. 2 is an exploded perspective view of a fixation device according to an embodiment of the invention.

As also shown in the exploded perspective view in FIG. 2, each pin support member 4 comprises an elongate body having a frame attachment portion 4' and a pin supporting portion 4". The frame attachment portion 4' is formed with an elongate through slot 8 to be displaceable attached to the stereotactic frame 2 by means of for example a screw joint. In this way the pin support member may be adjusted by being moved in its longitudinal direction, perpendicular to the plane of the stereotactic frame and in this way be adapted to the specific conditions associated with each patient. However, it is also feasible to attach the pin support member to the frame member in alternative ways, e.g. by a pivot hinge in which case the pin support member may be adjusted by pivoting in relation to the frame member.

The pin supporting portion 4" comprises a receiving formation in form of a through hole 9 for receiving a sleeve member 5. The through hole 9 is in this embodiment unthreaded and have smooth walls so as to receive the sleeve member 5 by press fit from the side of the pin support member which is adapted to be turned towards the head. To prevent the sleeve member 5 from passing through the hole 9 in the pin support member, the sleeve member 5 is formed like a seating having an abutment surface 10 perpendicular to the insert direction of the sleeve member 5, which is adapted to bear against a corresponding surface in the sleeve member. Flat surfaces 11 in the hole, being parallel with the insert direction, which interact with corresponding surfaces in the sleeve member, prevent the sleeve member from being rotated when in seated position.

The sleeve member 5 is formed with a mounting portion 12, which prevents the sleeve member from passing through the pin support member by abutment against the contact surface 10 and the inner surface of the pin support member, and prevents the sleeve member from rotating by interacting with the flat surfaces 11. It is also provided with an extending portion 13 which in the embodiment shown has a cylindrical shape. The sleeve member is also provided with a through bore 14 having internal threads.

The fixation pin 6 is formed with external threads over essentially its hole length, a tip 15 in its front or inner end and an internal engagement means 16 in the rear or outer end. The engagement means preferably is in the form of an internal polygonal structure, e.g. a hexagonal bore.

In FIGS. 3 and 4 the assembled fixation device 1 is shown in schematic, partly cut through, elevations of two different embodiments, being in use mounted on the stereotactic frame 2. The pin support member 4 is mounted on the frame 2 and adjusted in height by means of the slot 8 (as shown in FIG. 2). The sleeve member 5 is inserted in the through hole in the upper part of the pin support member. Finally, the fixation pin 6 is screwed into the bore of the sleeve member until its tip penetrates a small distance into the head of the patient for reliable fixation of the same.

The two embodiments illustrated in FIGS. 3 and 4 are used for fixation of two different sizes of heads, namely a small head in FIG. 3 and a considerable larger head in FIG. 4. To accomplish this in a favourable manner in accordance with the invention, the fixation device is equipped with sleeve members having different lengths in the two embodiments respectively. Thus, the fixation device in FIG. 3, for fixation of a small size head 3, is provided with a comparatively long sleeve member 5, whereas the fixation device in FIG. 4, for fixation of a large size head 3, is provided with a short sleeve member 5.

As evident from the drawings, the mounting portions 12 of the two embodiments of the sleeve member, are identical and have the same length. The extending portion on the other hand, is made with a longer length in the embodiment according to FIG. 3 an extends, in the seated position of the sleeve member, inwards beyond the inner boundaries of the pin support member. In this way the free protruding length of the fixation pins between the inner end of the sleeve member and the head, may be restricted even when fixation of a small sized head. Accordingly, the bending moment, resulting from the weight of the head, are restricted in the fixation pins. Instead a major part of the bending moment is transferred to the sleeve member, which is better adapted to bear that kind of load due to its larger cross section dimensions.

As seen in FIGS. 3 and 4, none of the fixation pins 6 have their outer ends protruding beyond the outer boundary of the pin support members 4, though the fixation pins are of the same length in the two embodiments. This is advantageous since only one or a few lengths of fixation pins are required for fixation of all existing sizes of heads. Instead a few lengths of sleeve members are provided for each fixation device, wherein at least one and normally two to five sleeve members are enough for reliably fixation of existing sizes of heads.

It will be appreciated that the invention has been illustrated with reference to an exemplary embodiment and that the invention can be varied in many different ways within the scope of the appended claims.

The invention claimed is:

1. A method for fixation of the head of a patient during neurological diagnosis, therapy or surgery, comprising the steps of:
    providing a fixation device comprising a pin support member, a sleeve member supported on the pin support member having an inner boundary and an outer boundary and including an internal threaded through bore, and an external threaded fixation pin having an inner end and an outer end received and supported in the threaded bore of the sleeve member having an inner end and an outer end, wherein the sleeve member, in a seated position in the pin support member, extends inwards from the pin support member towards the head during use to protrude beyond the inner boundary of said pin support member;
    choosing a fixation pin having an appropriate length in consideration of obtaining a sufficient threaded length of the fixation pin inside the sleeve member but avoiding protruding of the outer end of the fixation pin from the outer end of the sleeve member; and
    performing the fixation of the head by screwing the fixation pin into the threaded bore of the associated sleeve member until the inner end of the fixation pin bears against the head.

2. The method according to claim 1, comprising the step of providing interchangeable sleeve members in at least two different lengths.

3. The method according to claim 2, comprising the step to choose a sleeve member having an appropriate length in relation to the size of the head to be fixed, in consideration of avoiding protruding of the fixation pin beyond the outer boundary of the pin support member.

4. The method according to claim 3, comprising the step to choose a sleeve member having an appropriate length in relation to the size of the head to be fixed, in consideration of obtaining a suitable distance between an inner end of the sleeve member and the head, and hence a suitable free protruding length of the fixation pin between the sleeve member and the head.

5. The method according to claim 4, wherein choosing a sleeve member such that the distance between the inner end of the sleeve member and the head will amount to 0-30 mm.

6. The method according to claim 2, comprising the step to choose a sleeve member having an appropriate length in relation to the size of the head to be fixed, in consideration of obtaining a suitable distance between an inner end of the sleeve member and the head, and hence a suitable free protruding length of the fixation pin between the sleeve member and the head.

7. The method according to claim 6, wherein choosing a sleeve member such that the distance between the inner end of the sleeve member and the head will amount to 0-30 mm.

8. The method according to claim 6, wherein choosing a sleeve member such that the distance between the inner end of the sleeve member and the head will amount to 0-20 mm.

9. The method according to claim 6, wherein choosing a sleeve member such that the distance between the inner end of the sleeve member and the head will amount to 0-10 mm.

10. A device for fixation of a head of a patient during neurological diagnosis, therapy or surgery, said device comprising at least one fixation pin for fixation to the head, a sleeve member having an internally threaded through bore to at least partly receive and hold said fixation pin, and a pin support member having an inner boundary and an outer boundary for supporting said fixation pin and sleeve member, wherein the sleeve member extends inwards from said pin support member towards the head during use to protrude beyond the inner boundary of said pin support member, and wherein the sleeve member is exchangeable and is provided in at least two different lengths in order to allow adaptation of the sleeve member to the size of the head to improve the fixation of the head and avoid the fixation pin to protrude beyond the outer boundary of the pin support member when in a position for fixation.

11. A device according to claim 10, wherein the pin support member is formed with a through hole functioning as a seating for the sleeve member.

12. A device according to claim 11, wherein the sleeve member is attached to the pin support member by means of a press fit.

13. An assembly comprising at least three fixation devices according to claim 12, which are connected to a common frame member.

14. An assembly comprising at least three fixation devices according to claim 11, which are connected to a common frame member.

15. A device according to claim 10, wherein the sleeve member is manufactured from an electric insulating material.

16. An assembly comprising at least three fixation devices according to claim 15, which are connected to a common frame member.

17. An assembly comprising at least three fixation devices according to claim 10, which are connected to a common frame member.

18. An assembly comprising at least three fixation devices according to claim 10, which are connected to a common frame member.

* * * * *